United States Patent
Berge et al.

(10) Patent No.: US 9,295,683 B2
(45) Date of Patent: Mar. 29, 2016

(54) OMEGA-3 PHOSPHOLIPID SUPPLEMENTS FOR IMPROVED BRAIN MATURITY

(71) Applicant: AKER BIOMARINE ANTARCTIC AS, Stamsund (NO)

(72) Inventors: Kjetil Berge, Oslo (NO); Lena Burri, Oslo (NO)

(73) Assignee: AKER BIOMARINE ANTARCTIC AS, Stamsund (NO)

( * ) Notice: Subject to any disclaimer, the term of this patent is extended or adjusted under 35 U.S.C. 154(b) by 0 days.

(21) Appl. No.: 14/204,592

(22) Filed: Mar. 11, 2014

(65) Prior Publication Data

US 2014/0274968 A1 Sep. 18, 2014

Related U.S. Application Data

(60) Provisional application No. 61/783,574, filed on Mar. 14, 2013.

(51) Int. Cl.
| | |
|---|---|
| A61K 31/66 | (2006.01) |
| A61K 31/661 | (2006.01) |
| A61K 31/194 | (2006.01) |
| A61K 31/23 | (2006.01) |
| A23L 1/30 | (2006.01) |
| A23J 7/00 | (2006.01) |
| A23L 1/29 | (2006.01) |

(52) U.S. Cl.
CPC ............... *A61K 31/661* (2013.01); *A23J 7/00* (2013.01); *A23L 1/29* (2013.01); *A23L 1/30* (2013.01); *A23L 1/3006* (2013.01); *A61K 31/194* (2013.01); *A61K 31/23* (2013.01); *A23V 2002/00* (2013.01)

(58) Field of Classification Search
CPC ... A61K 31/194; A61K 31/23; A61K 31/661; A23V 2250/1868; A23V 2250/187; A23L 1/29; A23L 1/30; A23L 1/3006
USPC ........................................................ 514/120
See application file for complete search history.

(56) References Cited

U.S. PATENT DOCUMENTS

| | | | |
|---|---|---|---|
| 8,586,567 B2 * | 11/2013 | Sampalis ............... | A61K 31/07 514/120 |
| 2009/0074857 A1 | 3/2009 | Dror et al. | |
| 2011/0104297 A1 | 5/2011 | Bruheim | |
| 2011/0160161 A1 * | 6/2011 | Sampalis ............... | A61K 31/685 514/77 |
| 2011/0268811 A1 | 11/2011 | Minatelli | |
| 2014/0088043 A1 * | 3/2014 | Hoem ................... | A61K 31/685 514/77 |

FOREIGN PATENT DOCUMENTS

| | | |
|---|---|---|
| WO | 02/090560 | 11/2002 |
| WO | 03/011873 | 2/2003 |
| WO | 2005/037848 | 4/2005 |
| WO | 2005/038037 | 4/2005 |
| WO | 2006/054183 | 5/2006 |
| WO | 2008/117062 | 10/2008 |
| WO | 2009/027692 | 3/2009 |

OTHER PUBLICATIONS

NIH website, http://www.nimh.nih.gov/health/topics/attention-deficit-hyperactivity-disorder-adhd/index.shtml, Mental Health Information, "Attention Deficit Hyperactivity Disorder (ADHD)", pp. 1-10.*
Committee on Quality Improvement, Subcommittee on Attention-Deficit/Hyperactivity Disorder, "Clinical Practice Guideline: Diagnosis and Evaluation of the Child With Attention-Deficit/Hyperactivity Disorder", 2000, Pediatrics, 105(5), pp. 1158-1170.*
Antalis CJ, Stevens LJ, Campbell M, Pazdro R, Ericson K, Burgess JR: Omega-3 fatty acid status in attention-deficit/hyperactivity disorder. Prostaglandins, leukotrienes, and essential fatty acids 2006, 75:299-308.
Arterburn, Linda M., et al., "Bioequivalence of Docosahexaenoic Acid from Different Algal Oils in Capsules and in a DHA-Fortified Food," Lipids, vol. 42, No. 11, Aug. 23, 2007, pp. 1011-1024.
Burgess JR, Stevens L, Zhang W, Peck L: Long-chain polyunsaturated fatty acids in children with attention-deficit hyperactivity disorder. Am J Clin Nutr 2000, 71:327S-330S.
Chalon S: The role of fatty acids in the treatment of ADHD. Neuropharmacology 2009, 57:636-639.
Colter AL, Cutler C, Meckling KA: Fatty acid status and behavioural symptoms of attention deficit hyperactivity disorder in adolescents: a case-control study. Nutr J 2008, 7:8. 278.
Furia and Pellanca, Fenaroli's Handbook of Flavor Ingredients, The Chemical Rubber Company, Cleveland, Ohio (1971).
Harris, W., Am J Clin Nutr (2008) 87(6); pp. 1997S-2002S.
Jan Philipp Schuchardt et al., "Incorporation of EPA and DHA into plasma phospholipids in response to different omega-3 fatty acid formulations—a comparative bioavailability study of fish oil vs. krill oil," Lipids in Health and Disease, Biomed Central, London, GB, vol. 10, No. 1, Aug. 22, 2011, p. 145.
Kidd, P.M., "Omega-3 DHA and EPA for cognition, behavior, and mood: Clinical findings and structural-functional synergies with cell membrane phospholipids," Alternative Medicine Review, Thorne Research Inc., Sandpoint, US, vol. 12, No. 3, Sep. 1, 2007, pp. 207-227.
Mann CA, Lubar JF, Zimmerman AW Miller CA, Muenchen RA: Quantitative analysis of EEG in boys with attention-deficit-hyperactivity disorder: controlled study with clinical implications. Pediatric neurology 1992, 8:30-36.
Monastra VJ, Lubar JF, Linden M: The development of a quantitative electroencephalographic scanning process for attention deficit-hyperactivity disorder: reliability and validity studies. Neuropsychology 2001, 15:136-144.

(Continued)

*Primary Examiner* — My-Chau T Tran
(74) *Attorney, Agent, or Firm* — Casimir Jones S.C.

(57) ABSTRACT

The invention relates to omega-3 phospholipid supplements for use in adolescents, and in particular to use omega-3 phospholipid supplements to improve or support brain maturity age. In preferred embodiments, the omega-3 phospholipid is krill oil.

15 Claims, 4 Drawing Sheets

(56) References Cited

OTHER PUBLICATIONS

Phleger et al., Comp. Biochem. Physiol. 131B (2002), p. 733.

Raz R, Gabis L: Essential fatty acids and attention-deficit-hyperactivity disorder:a systematic review. Dev Med Child Neurol 2009, 51:580-592. 289.

Remington's Pharmaceutical Sciences, 18th edition, Mack Publishing, pp. 1288-1300 (1990).

Schuchardt JP, Huss M, Stauss-Grabo M, Hahn A: Significance of long-chain polyunsaturated fatty acids (PUFAs) for the development and behaviour of children. Eur J Pediatr 2010, 169:149-164.

Stevens L, Zhang W, Peck L, Kuczek T, Grevstad N, Mahon A, Zentall SS, Arnold LE, Burgess JR: EFA supplementation in children with inattention, hyperactivity, and other disruptive behaviors. Lipids 2003, 38:1007-1021.

Vaisman N, Kaysar N, Zaruk-Adasha Y, Pelled D, Brichon G, Zwingelstein G, Bodennec J: Correlation between changes in blood fatty acid composition and visual sustained attention performance in children with inattention: effect of dietary n-3 fatty acids containing phospholipids. Am J Clin Nutr 2008, 87:1170-1180.

Virtue, et al., Mar. Biol. (1996) 126, pp. 521-527.

Wang, Q., et al., "Analysis of DHA-rich phospholipids from egg and squid Sthenoteuthis oualaniensis," Journal of Food Composition and Analysis, Academic Press, London, GB, vol. 21, No. 4, Jun. 1, 2008, pp. 356-359.

International Search Report and Written Opinion, International Patent Application No. PCT/IB2014/001052, mailed Apr. 13, 2015.

Suzuki, H: "Health effects of fish oil.", Journal of the Japan Oil Chemists Society, vol. 48, No. 10, 2000, English Abstract.

Bryhn, M. "Food for thoughts—marine omega-3 fatty acids and mental health.", Innovations in Food Technology, 2002, No. 12, pp. 52-56.

Connor et al., "The importance of fish and docosahexaenoic acid in Alzheimer disease.", American Journal of Clinical Nutrition, 2007, vol. 85, No. 4, p. 929.

Vedin I. et al., "Effects of docosahexaenoic acid-rich n-3 fatty acid supplementation on cytokine release from blood mononuclear leukocytes: the OmegAD study", American Journal of Clinical Nutrition, vol. 87, No. 6, 2008.

Dyall et al., "Dietary enrichment with omega-3 polyunsaturated fatty acids reverses age-related decreases in GluR2 and NR2B glutamate receptor subunits in rat forebrain.", Neurobiology of Aging, 2007, vol. 28, No. 3, pp. 424-439.

\* cited by examiner

# OMEGA-3 PHOSPHOLIPID SUPPLEMENTS FOR IMPROVED BRAIN MATURITY

CROSS-REFERENCE TO RELATED APPLICATIONS

This application claims priority to U.S. Provisional Patent Application No. 61/783,574, filed Mar. 14, 2013, the contents of which are incorporated by reference in its entirety.

FIELD OF THE INVENTION

The invention relates to omega-3 phospholipid supplements for use in adolescents, and in particular to use omega-3 phospholipid supplements to improve brain maturity age.

BACKGROUND OF THE INVENTION

Krill is a small crustacean which lives in all the major oceans world-wide. For example, it can be found in the Pacific Ocean (*Euphausia pacifica*), in the Northern Atlantic (*Meganyctiphanes norvegica*) and in the Southern Ocean off the coast of Antarctica (*Euphausia superba*). Krill is a key species in the ocean as it is the food source for many animals such as fish, birds, sharks and whales. Krill can be found in large quantities in the ocean and the total biomass of Antarctic krill (*E. superba*) is estimated to be in the range of 300-500 million metric tons. Antarctic krill feeds on phytoplankton during the short Antarctic summer. During winter, however, its food supply is limited to ice algae, bacteria, marine detritus as well as depleting body protein for energy. Virtue et al., Mar. Biol. (1996) 126, 521-527. For this reason, the nutritional values of krill vary during the season and to some extent annually. Phleger et al., Comp. Biochem. Physiol. 131B (2002) 733.

The long-chain omega-3 polyunsaturated fatty acids DHA and EPA are popularly called omega-3. Supplementary intake of omega-3 is recommended in the western world, due to generally low dietary intake and omega-3's health-promoting benefits. Benefits attributed to omega-3 include reduced risk and improved treatment outcomes regarding cardiovascular disease and inflammatory joint diseases. Better brain and central nervous system development, improved cognitive functioning, and improved skin health are additional benefits. Research indicates that even more omega-3 benefits for individuals will be identified and that greater intake can lead to better general health in western, industrialized cultures.

The omega-3 in krill oil is mainly in the omega-3 phospholipid form, which research suggests is a preferred dietary supplement when compared to omega-3 in triglyceride form. Marine omega-3 in dietary supplements is mostly derived from fish, such as fish body oil and cod liver oil, which provide omega-3 in triglyceride form. The omega-3 obtained from eating fatty fish such as salmon also provides some omega-3 in the phospholipid form.

SUMMARY OF THE INVENTION

The invention relates to omega-3 phospholipid supplements for use in adolescents, and in particular to use omega-3 phospholipid supplements to improve or support brain maturity age.

In some embodiments, the present invention provides methods of improving or supporting brain maturity age in a subject in need thereof comprising administering an omega-3 phospholipid supplement to the subject under conditions such that the brain maturity age of the subject is improved. In some embodiments, the omega-3 phospholipid supplement is a krill oil, fish oil, fish roe oil, or fish byproduct oil. In some embodiments, the krill oil comprises from about 35% to 60% phospholipids on a w/w basis; from about 20% to 45% triglycerides on a w/w basis; and from about 50 to about 2500 mg/kg astaxanthin. In some embodiments, the composition comprises from about 3% to 10% ether phospholipids on a w/w basis, so that the total amount of ether phospholipids and non-ether phospholipids in the composition is from about 48% to 60% on a w/w basis. In some embodiments, the composition comprises from about 25% to 30% omega-3 fatty acids as a percentage of total fatty acids and wherein from about 80% to 90% of the omega-3 fatty acids are attached to the phospholipids. In some embodiments, the composition comprises from about 100 to about 2500 mg/kg astaxanthin. In some embodiments, the omega-3 supplement comprises from about 1% to about 10% w/w ether phospholipids; from about 27% to 50% w/w non-ether phospholipids so that the amount of total phospholipids in the composition is from about 30% to 60% w/w; from about 20% to 50% w/w triglycerides; from about 100 to about 2500 mg/kg astaxanthin; and from about 20% to 35% omega-3 fatty acids as a percentage of total fatty acids in the composition, wherein from about 70% to 95% of the omega-3 fatty acids are attached to the phospholipids. In some embodiments, the omega-3 is selected from EPA and DHA and combinations thereof.

In some embodiments, the subject is an adolescent. In some embodiments, the adolescent is a male. In some embodiments, the administration is oral. In some embodiments, the omega-3 phospholipid supplemented is administered a daily dosage of from about 3 grams to about 6 grams per day. In some embodiments, the daily dose is administered in two doses of from 1.5 to 3 grams in the morning and evening. In some embodiments, the subject has been diagnosed with ADHD. In some embodiments, brain maturation age is calculated by comparison of EEG measurements with reference EEG measurements.

In some embodiments, the present invention provides for use of an omega-3 phospholipid supplement to improve or support brain maturity age of a subject in need thereof. In some embodiments, the omega-3 phospholipid supplement is a krill oil, fish oil, fish roe oil, or fish byproduct oil. In some embodiments, the krill oil comprises from about 35% to 60% phospholipids on a w/w basis; from about 20% to 45% triglycerides on a w/w basis; and from about 50 to about 2500 mg/kg astaxanthin.

DEFINITIONS

Figure 1:
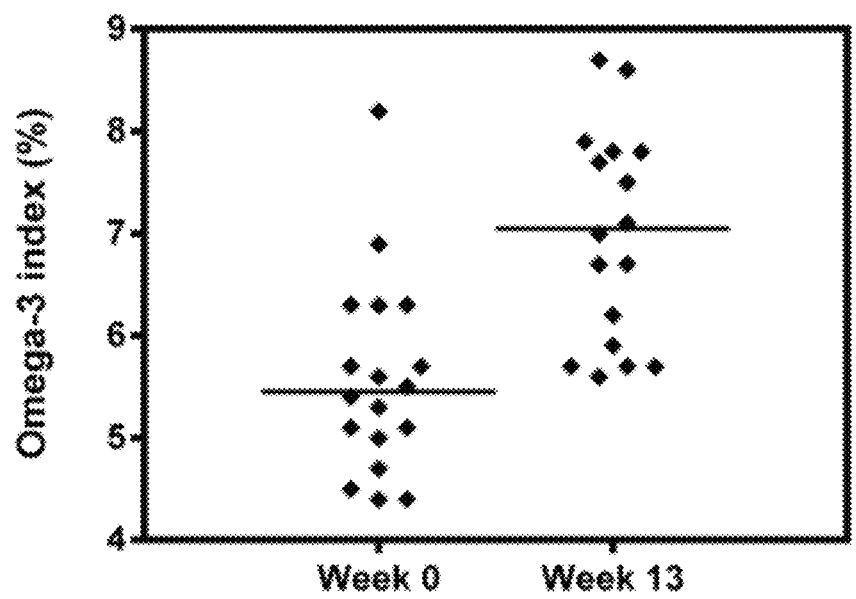
FIG. 1. Increase of omega-3 index after 13 weeks daily intake of 4 g krill oil (n=18).

As used herein, "phospholipid" refers to an organic compound having the following general structure:

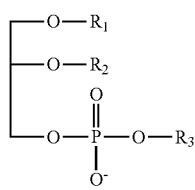

wherein R1 is a fatty acid residue or —H, R2 is a fatty acid residue or —H, and R3 is a —H or nitrogen containing moiety selected from, for example, choline, serine, ethanolamine and inositol moieties. Preferably, R1 and R2 cannot simultaneously be —H. When R3 is an —H, the compound is a diacylglycerophosphate, while when R3 is a nitrogen-containing compound, the compound is a phosphatide such as lecithin (i.e., phosphatidylcholine), cephalin, phosphatidylethanolamine, phosphatidylserine or plasmalogen.

An "ether phospholipid" as used herein refers to a phospholipid having an ether bond at position 1 of the glycerol backbone. Examples of ether phospholipids include, but are not limited to, alkylacylphosphatidylcholine (AAPC), lyso-alkylacylphosphatidylcholine (LAAPC), and alkylacylphosphatidylethanolamine (AAPE). A "non-ether phospholipid" is a phospholipid that does not have an ether bond at position 1 of the glycerol backbone.

As used herein, the term omega-3 fatty acid refers to polyunsaturated fatty acids that have the final double bond in the hydrocarbon chain between the third and fourth carbon atoms from the methyl end of the molecule. Non-limiting examples of omega-3 fatty acids include, 5,8,11,14,17-eicosapentaenoic acid (EPA), 4,7,10,13,16,19-docosahexanoic acid (DHA) and 7,10,13,16,19-docosapentanoic acid (DPA).

As used herein, the term "omega-3 phospholipid" refers to phospholipids that at either the R1 and/or R2 positions comprise polyunsaturated fatty acids that have the final double bond in the hydrocarbon chain between the third and fourth carbon atoms from the methyl end of the molecule. Non-limiting examples of omega-3 fatty acids include, 5,8,11,14, 17-eicosapentaenoic acid (EPA), 4,7,10,13,16,19-docosahexanoic acid (DHA) and 7,10,13,16,19-docosapentanoic acid (DPA).

As used herein, the term "omega-3 phospholipid supplement" refers to a composition comprising natural or synthetic omega-3 phospholipids.

As used herein, astaxanthin refers to the following chemical structure:

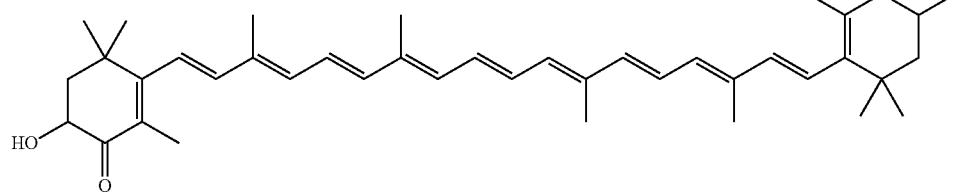

As used herein, astaxanthin esters refer to an astaxanthin molecule where a fatty acid is esterified to one or two of the OH groups in the molecule.

As used herein, the term w/w (weight/weight) refers to the amount of a given substance in a composition on weight basis. For example, a composition comprising 50% w/w phospholipids means that the mass of the phospholipids is 50% of the total mass of the composition (i.e., 50 grams of phospholipids in 100 grams of the composition, such as an oil).

As used herein, the term "fresh krill" refers to krill that is has been harvested less than about 12, 6, 4, 2 or preferably 1 hour prior to processing. "Fresh krill" is characterized in that products made from the fresh krill such as coagulum comprise less than 1 mg/100 g TMA, volatile nitrogen or Trimetylamine oxide-N, alone or in combination, and less than 1 g/100 g lysophosphatidylcholine.

As used herein the term "omega-3 index" is defined as the sum of EPA and DHA in erythrocyte membranes and is expressed as a percentage of total erythrocyte fatty acids. Harris W., Am J Clin Nutr (2008) 87(6); 1997S-2002S.

DETAILED DESCRIPTION OF THE INVENTION

The invention relates to omega-3 phospholipid supplements for use in adolescents, and in particular to use omega-3 phospholipid supplements to improve brain maturity age.

Attention Deficit/Hyperactivity Disorder (ADHD) is a neuropsychiatric condition that affects 3-7% of school children. ADHD is characterized by inattention, hyperactivity, and impulsivity prior to the age of 7 and often extends throughout adolescence and adulthood [1]. If left untreated it can increase the risk of social problems, failure in school, and psychopathology later in life [2].

Individuals with ADHD are found to have abnormal plasma phospholipids and red blood cell phospholipid fatty acids [3, 4]. Docosahexaenoic acid (DHA) levels in red blood cells are consistently found lower in individuals with ADHD compared to controls [4], which was found to correlate with increased hyperactivity [5]. It was suggested that increased degradation of omega-3 fatty acids might be the reason for low omega-3 fatty acid levels in ADHD patients [6].

As lipids make up about 60% of the dry weight of the brain and DHA is one of the most abundant fatty acids in the brain, retina and nervous system [7], several studies have investigated the effect of omega-3 fatty acid supplementation. Some, but not all, studies have reported improvements of ADHD symptoms [8-11]. Of note is one study comparing the effect of omega-3 fatty acid supplementation in different molecular forms, i.e. fatty acids bound to phospholipids or to triglycerides [12]. In this study, the phospholipid omega-3 treatment improved the test of variables of attention (TOVA) scores most, which correlates with reports finding increased brain fatty acid accretion, when delivered in phospholipid over triglyceride form [8, 13-15].

A supplement that is known to mainly supply its omega-3 fatty acids in the form of phospholipids is krill oil. Krill oil is extracted from Antarctic krill (*Euphausia superba*), a shrimp-like crustacean living in huge swarms in the Southern Ocean.

It was previously shown that hill oil significantly increases DHA levels in the brains of rats more so than by fish oil supplementation [13]. It was therefore of interest to test krill oil for the management of ADHD symptoms in children.

EEG (electroencephalography) measures the electrical activity in the brain. Direct measures of brain function can be used as non-invasive, objective biomarkers of neural mechanisms associated with fatty acids and have been studied previously as indicators of response to treatment by stimulant medications [16]. It has been shown that resting state EEG correlates with red blood cell long-chain fatty acids, memory performance and age in adolescent boys with ADHD [17]. Several studies have indicated that EEG measurements are capable of correctly discriminating between ADHD and control individuals with 73-93% accuracy [18-21]. Magnetic resonance imaging (MRI) studies of ADHD children support the EEG findings by showing abnormalities in the cortex and some subcortical areas [22-25].

The EEG of school age children changes significantly from one year to another. This systematic development in EEG activity has been found to change differently in children with ADHD, indicating anomalies in brain development [26, 27]. Imaging studies have demonstrated this difference in brain development of ADHD children as a delay rather than a deviance of normal brain maturation in the regional cortical maturation. MRI measures of cortical thickness showed an average of three years delay of cortical maturity in ADHD children compared to controls [28]. By comparing the brain maturity assessed by EEG measurements with a database of control and ADHD subjects, we were able to investigate the effect of krill oil on the developmental stage of the brain in ADHD boys.

In preferred embodiments, the methods of the present invention utilize omega-3 phospholipids to improve brain maturity are in adolescents, preferably male adolescents. The omega-3 phospholipids may be naturally occurring, such as those obtained from krill (i.e., krill oil) or synthetic, such as those made by an enzymatic process. Suitable processes for synthetic omega-3 phospholipids are described in WO06/054183, WO02090560, WO05/037848, and WO05/038037, all of which are incorporated herein by reference. Suitable processes for producing krill oil include extraction with polar solvents such as ethanol, supercritical fluid extraction, extraction with non-polar organic solvents such as acetone, cold pressing, etc. See, e.g., WO2009/027692, WO2008/117062, WO2003/011873, all of which are incorporated herein by reference. In some embodiments, krill oil is extracted from the denatured krill meal. In some embodiments, the krill oil is extracted by contacting the krill meal with ethanol. In some embodiments, krill is then extracted with a ketone solvent such as acetone. In other embodiments, the krill oil is extracted by one or two step supercritical fluid extraction.

In some embodiments, the present invention utilizes an omega-3 phospholipid composition, preferably a krill oil composition, marine phospholipids form fish roe, fish or fish by-products, or synthetic omega-3 phospholipid, and more preferably a *Euphausia superba* krill oil composition, comprising from about 40% to about 60% w/w phospholipids, preferably from about 45% to 55% w/w phospholipids. In some embodiments, the composition comprise from about 50 mg/kg astaxanthin to about 2500 mg/kg astaxanthin, preferably from about 1000 to about 2200 mg/kg astaxanthin, more preferably from about 1500 to about 2200 mg/kg astaxanthin. In some preferred embodiments, the compositions comprise greater than about 1000, 1500, 1800, 1900, 2000, or 2100 mg/kg astaxanthin. In some preferred embodiments, the omega-3 phospholipid compositions of the present invention comprise from about 1%, 2%, 3% or 4% to about 8%, 10%, 12% or 15% w/w ether phospholipids or greater than about 4%, 5%, 6%, 7%, 8%, 9% or 10% ether phospholipids. In some embodiments the ether phospholipids are preferably alkylacylphosphatidylcholine, lyso-alkylacylphosphatidylcholine, alkylacylphosphatidyl-ethanolamine or combinations thereof. In some embodiments, the omega-3 phospholipid compositions comprise from about 1%, 2%, 3% or 4% to about 8%, 10%, 12% or 15% w/w ether phospholipids and from about 30%, 33%, 40%, 42%, 45%, 48%, 50%, 52%, 54%, 55% 56%, 58% to about 60% non-ether phospholipids so that the total amount of phospholipids (both ether and non-ether phospholipids) ranges from about 40% to about 60%. One of skill in the art will recognize that the range of 40% to 60% total phospholipids, as well as the other ranges of ether and non-ether phospholipids, can include other values not specifically listed within the range.

In further embodiments, the compositions comprise from about 20% to 45% w/w triglycerides; and from about 50 to about 2500 mg/kg astaxanthin. In some embodiments, the compositions comprise from about 20% to 35%, preferably from about 25% to 35%, omega-3 fatty acids as a percentage of total fatty acids in the composition, wherein from about 70% to 95%, or preferably from about 80% to 90% of the omega-3 fatty acids are attached to the phospholipids. In some embodiments, the present invention provides encapsulated *Euphausia superba* krill oil compositions.

The present invention is not limited to the presence of any particular omega-3 fatty acid residues in the omega-3 phospholipid composition. In some preferred embodiments, the omega-3 phospholipid comprises EPA and DHA residues. In some embodiments, the omega-3 phospholipid compositions comprise less than about 5%, 4%, 3% or preferably 2% free fatty acids on a weight/weight (w/w) basis. In some embodiments, the omega-3 phospholipid compositions comprise less than about 25%, 20%, 15%, 10% or 5% triglycerides (w/w). In some embodiments, the krill oil compositions comprise greater than about 30%, 40%, 45%, 50%, 55%, 60%, or 65% phosphatidyl choline (w/w). In some embodiments, the omega-3 phospholipid compositions comprise greater than about 100, 200, 300, 400, or 500 mg/kg astaxanthin esters and up to about 700 mg/kg astaxanthin esters. In some embodiments, the present invention provides omega-3 phospholipid compositions comprising at least 500, 1000, 1500, 2000, 2100, or 2200 mg/kg astaxanthin esters and at least 36% (w/w) omega-3 fatty acids. In some embodiments, the krill oil compositions of the present invention comprise less than about 1.0 g/100 g, 0.5 g/100 g, 0.2 g/100 g or 0.1 g/100 g total cholesterol.

In some embodiments, the compositions of this invention (such as those described in the preceding paragraphs) are contained in acceptable excipients and/or carriers for oral consumption. The actual form of the carrier, and thus, the composition itself, is not critical. The carrier may be a liquid, gel, gelcap, capsule, powder, solid tablet (coated or non-coated), tea, or the like. The composition is preferably in the form of a tablet or capsule and most preferably in the form of a soft gel capsule. Suitable excipient and/or carriers include maltodextrin, calcium carbonate, dicalcium phosphate, tricalcium phosphate, microcrystalline cellulose, dextrose, rice flour, magnesium stearate, stearic acid, croscarmellose sodium, sodium starch glycolate, crospovidone, sucrose, vegetable gums, lactose, methylcellulose, povidone, carboxymethylcellulose, corn starch, and the like (including mixtures thereof). Preferred carriers include calcium carbonate, magnesium stearate, maltodextrin, and mixtures thereof. The various ingredients and the excipient and/or carrier are mixed and formed into the desired form using conventional techniques. The tablet or capsule of the present invention may be coated with an enteric coating that dissolves at a pH of about 6.0 to 7.0. A suitable enteric coating that dissolves in the small intestine but not in the stomach is cellulose acetate phthalate. Further details on techniques for formulation for and administration may be found in the latest edition of Remington's Pharmaceutical Sciences (Maack Publishing Co., Easton, Pa.).

The dietary supplement may comprise one or more inert ingredients, especially if it is desirable to limit the number of calories added to the diet by the dietary supplement. For example, the dietary supplement of the present invention may also contain optional ingredients including, for example, herbs, vitamins, minerals, enhancers, colorants, sweeteners, flavorants, inert ingredients, and the like. For example, the dietary supplement of the present invention may contain one or more of the following: ascorbates (ascorbic acid, mineral ascorbate salts, rose hips, acerola, and the like), dehydroepiandosterone (DHEA), Fo-Ti or Ho Shu Wu (herb common to traditional Asian treatments), Cat's Claw (ancient herbal ingredient), green tea (polyphenols), inositol, kelp, dulse, bioflavinoids, maltodextrin, nettles, niacin, niacinamide, rosemary, selenium, silica (silicon dioxide, silica gel, horsetail, shavegrass, and the like), spirulina, zinc, and the like. Such optional ingredients may be either naturally occurring or concentrated forms.

In some embodiments, the dietary supplements further comprise vitamins and minerals including, but not limited to, calcium phosphate or acetate, tribasic; potassium phosphate, dibasic; magnesium sulfate or oxide; salt (sodium chloride); potassium chloride or acetate; ascorbic acid; ferric orthophosphate; niacinamide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; vitamin D3; cyanocobalamin; sodium selenite; copper sulfate; vitamin A; vitamin C; inositol; potassium iodide. Suitable dosages for vitamins and minerals may be obtained, for example, by consulting the U.S. RDA guidelines.

In further embodiments, the compositions comprise at least one food flavoring such as acetaldehyde (ethanal), acetoin (acetyl methylcarbinol), anethole (parapropenyl anisole), benzaldehyde (benzoic aldehyde), N butyric acid (butanoic acid), d or 1 carvone (carvol), cinnamaldehyde (cinnamic aldehyde), citral (2,6 dimethyloctadien 2,6 al 8, geranial, neral), decanal (N decylaldehyde, capraldehyde, capric aldehyde, caprinaldehyde, aldehyde C 10), ethyl acetate, ethyl butyrate, 3 methyl 3 phenyl glycidic acid ethyl ester (ethyl methyl phenyl glycidate, strawberry aldehyde, C 16 aldehyde), ethyl vanillin, geraniol (3,7 dimethyl 2,6 and 3,6 octadien 1 ol), geranyl acetate (geraniol acetate), limonene (d, l, and dl), linalool (linalol, 3,7 dimethyl 1,6 octadien 3 ol), linalyl acetate (bergamol), methyl anthranilate (methyl 2 aminobenzoate), piperonal (3,4 methylenedioxy benzaldehyde, heliotropin), vanillin, alfalfa (*Medicago sativa* L.), allspice (*Pimenta officinalis*), ambrette seed (*Hibiscus abelmoschus*), angelic (*Angelica archangelica*), Angostura (*Galipea officinalis*), anise (*Pimpinella anisum*), star anise (*Illicium verum*), balm (*Melissa officinalis*), basil (*Ocimum basilicum*), bay (*Laurus nobilis*), calendula (*Calendula officinalis*), (*Anthemis nobilis*), capsicum (*Capsicum frutescens*), caraway (*Carum carvi*), cardamom (*Elettaria cardamomum*), cassia, (*Cinnamomum cassia*), cayenne pepper (*Capsicum frutescens*), Celery seed (*Apium graveolens*), chervil (*Anthriscus cerefolium*), chives (*Allium schoenoprasum*), coriander (*Coriandrum sativum*), cumin (*Cuminum cyminum*), elder flowers (*Sambucus canadensis*), fennel (*Foeniculum vulgare*), fenugreek (*Trigonella foenum graecum*), ginger (*Zingiber officinale*), horehound (*Marrubium vulgare*), horseradish (*Armoracia lapathifolia*), hyssop (*Hyssopus officinalis*), lavender (*Lavandula officinalis*), mace (*Myristica fragrans*), marjoram (*Majorana hortensis*), mustard (*Brassica nigra, Brassica juncea, Brassica hirta*), nutmeg (*Myristica fragrans*), paprika (*Capsicum annuum*), black pepper (*Piper nigrum*), peppermint (*Mentha piperita*), poppy seed (*Papaver somniferum*), rosemary (*Rosmarinus officinalis*), saffron (*Crocus sativus*), sage (*Salvia officinalis*), savory (*Satureia hortensis, Satureia montana*), sesame (*Sesamum indicum*), spearmint (*Mentha spicata*), tarragon (*Artemisia dracunculus*), thyme (*Thymus vulgaris, Thymus serpyllum*), turmeric (*Curcuma longa*), vanilla (*Vanilla planifolia*), zedoary (*Curcuma zedoaria*), sucrose, glucose, saccharin, sorbitol, mannitol, aspartame. Other suitable flavoring are disclosed in such references as Remington's Pharmaceutical Sciences, 18th Edition, Mack Publishing, p. 1288-1300 (1990), and Furia and Pellanca, Fenaroli's Handbook of Flavor Ingredients, The Chemical Rubber Company, Cleveland, Ohio, (1971), known to those skilled in the art.

In other embodiments, the compositions comprise at least one synthetic or natural food coloring (e.g., annatto extract, astaxanthin, beet powder, ultramarine blue, canthaxanthin, caramel, carotenal, beta carotene, carmine, toasted cottonseed flour, ferrous gluconate, ferrous lactate, grape color extract, grape skin extract, iron oxide, fruit juice, vegetable juice, dried algae meal, tagetes meal, carrot oil, corn endosperm oil, paprika, paprika oleoresin, riboflavin, saffron, tumeric, tumeric and oleoresin).

In still further embodiments, the compositions comprise at least one phytonutrient (e.g., soy isoflavonoids, oligomeric proanthcyanidins, indol 3 carbinol, sulforaphone, fibrous ligands, plant phytosterols, ferulic acid, anthocyanocides, triterpenes, omega 3/6 fatty acids, conjugated fatty acids such as conjugated linoleic acid and conjugated linolenic acid, polyacetylene, quinones, terpenes, cathechins, gallates, and quercitin). Sources of plant phytonutrients include, but are not limited to, soy lecithin, soy isoflavones, brown rice germ, royal jelly, bee propolis, acerola berry juice powder, Japanese green tea, grape seed extract, grape skin extract, carrot juice, bilberry, flaxseed meal, bee pollen, *ginkgo biloba*, primrose (evening primrose oil), red clover, burdock root, dandelion, parsley, rose hips, milk thistle, ginger, Siberian ginseng, rosemary, curcumin, garlic, lycopene, grapefruit seed extract, spinach, and broccoli.

In still other embodiments, the compositions comprise at least one vitamin (e.g., vitamin A, thiamin (B1), riboflavin (B2), pyridoxine (B6), cyanocobalamin (B12), biotin, ascorbic acid (vitamin C), retinoic acid (vitamin D), vitamin E, folic acid and other folates, vitamin K, niacin, and pantothenic acid). In some embodiments, the particles comprise at least one mineral (e.g., sodium, potassium, magnesium, calcium, phosphorus, chlorine, iron, zinc, manganese, flourine, copper, molybdenum, chromium, selenium, and iodine). In some particularly preferred embodiments, a dosage of a plurality of particles includes vitamins or minerals in the range of the recommended daily allowance (RDA) as specified by the United States Department of Agriculture. In still other embodiments, the particles comprise an amino acid supplement formula in which at least one amino acid is included (e.g., 1-carnitine or tryptophan).

EXPERIMENTAL

Methods

Study Design

This single-center, open-label, multi-dose study was conducted by researchers at Mentis Cura, Iceland (www.mentiscura.is) in cooperation with the Department of child and adolescent psychiatry, Landspitali Hospital, Iceland. 20 male individuals between 7-12 y of age which were previously diagnosed with ADHD were recruited into the study. The children were all diagnosed by a child psychiatrist with K-SADS, a semistructured diagnostic interview designed to assess current and past episodes of psychopathology according to the Diagnostic and Statistical Manual of Mental Disorders (DSM-IV) criteria [29]. The participants were instructed not to change their regular diet, especially with respect to fish products. All participants were living in the area of Reykjavik, Iceland. There were two visits, one before starting treatment with krill oil (Visit 1, Week 0) and one visit after krill oil treatment was finished (Visit 2, Week 13). EEG was measured at both visits. The study period was during summer when there was no school. The participants on medical treatment had a washout period before visit 1 and visit 2, during which they received no medication. The wash-out period was 24 hours for methylphenidate and 48 hours for atomoxetin. Of the 20 subjects enrolled, 18 individuals completed the trial. In the interim between the two visits the 115 participants were instructed to take the daily dose of 4 g krill oil, 2 g in the morning and 2 g in the evening. The krill oil used in the study was obtained from Aker BioMarine ASA, Oslo, Norway (Superba™ Krill oil) and a detailed composition of the krill oil used is listed in Table 1. The study protocol was approved by the Icelandic National Bioethics Committee and written informed consent was obtained from all parents or guardians.

TABLE 1

Composition of krill oil.

|  | g/100 g | Content in 4 g krill oil (mg) |
|---|---|---|
| Phosphatidylcholine | 46 | 1 840 |
| Total polar lipids | 49 | 1 960 |
| Total neutral lipids | 39.6 | 1 584 |
| EPA | 13.1 | 524 |
| DHA | 6.6 | 264 |
| Total omega-3 fatty acids | 2.3 | 920 |
| Total omega-6 fatty acids | 1.6 | 64 |

DHA, docosahexaenoic acid; EPA, eicosapentaenoic acid

Omega-3 Index Measurements

Blood samples were collected from subjects at both visits. At each of the visits, a blood-drop was taken from a fingertip and collected on a filter paper. The cards were allowed to dry at room temperature for 2-4 hours and thereafter put into a sealed aluminum bag containing desiccant until analysis. They were stored at −80° C. until shipment on dry ice for omega-3 index measurements at Vitas AS, Oslo, Norway. Fatty acids were identified by comparison with known standards, and an external standard containing known amounts of fatty acid methyl esters was included in each run to correct for differences in fatty acid response factors. Fatty acid levels were expressed as weight percentage of total fatty acid methyl esters, and the omega-3 index is given as the percentage of eicosapentaenoic acid (EPA), DHA and docosapentaenoic acid (DPA) in red blood cell fatty acids.

EEG Measurements

At both visits, the EEG was recorded for 11 minutes. The IS 10-20 system was used for electrode placement. The following 19 electrodes were used: Fp1, Fp2, F3, F4, F7, F8, Fz, T3, T4, T5, T6, C3, C4, Cz, P3, P4, Pz, O1 and O2. The average potential was used as a reference. Two bipolar electrooculography channels were applied to monitor artifacts. The subjects were alerted if they became visibly drowsy. The EEG protocol was as follows: in the first three minutes the subject was at rest with eyes open, then five minutes with alternating eyes closed and eyes open, and finally three minutes at rest with eyes closed. The EEGs were measured using the NicoletOne nEEG Module from NatusMedical®. Subsequent analysis was done in the Matlab environment from The MathWorks®.

EEG Data Analysis

Mentis Cura has constructed a large database of EEG measurements and used statistical pattern recognition (SPR) with a large number of EEG features to analyze the EEGs. The reliability of the EEG features used in this study has already been investigated [30]. By mapping the brain activity of a group of healthy children age 6 to 14, their signals can be linked to an age related index developed by Mentis Cura, called brain maturity age (BMA). The conversion of EEG signals into the BMA will be explained in detail in an upcoming publication. The BMA is designed to closely correspond to the actual age of the subject, if the cortex of the subject has developed normally. If however, the brain of the subject has not matured normally (as is the case in ADHD subjects), then the BMA is expected to be lower than the actual age of the subject. The comparison of BMA and the actual age of an ADHD subject gives insight into the severity of the disorder. 156

Interviews

Parents or guardians of the subjects were contacted every 2 weeks to be interviewed. In total, there were 108 interviews with 6 interviews for each participant. The questions were "Have you observed changes in: attention, distraction, hyperactivity, irritability, proneness to anger, and communication problems?" The possible answers were: "less", "unchanged", or "more". In addition, the subjects were asked if they had generally felt positive effects, or if they had generally felt negative effects.

Results

Of the 20 subjects that were enrolled in the study, 18 completed it. 1 subject terminated the participation after 5 weeks due to unrelated health reasons and 1 subject withdrew from the 168 study due to troubles swallowing the capsules.

Omega-3 Index

After 13 weeks of treatment with krill oil, the omega-3 index, which is a measure of the percentage of EPA, DHA and DPA in the membranes of red blood cells, increased from 5.6±1.0 to 7.1±1.1 (FIG. 1).

BMA Vs Age for Normal and ADHD Groups in the Mentis Cura Database

Figure 2:
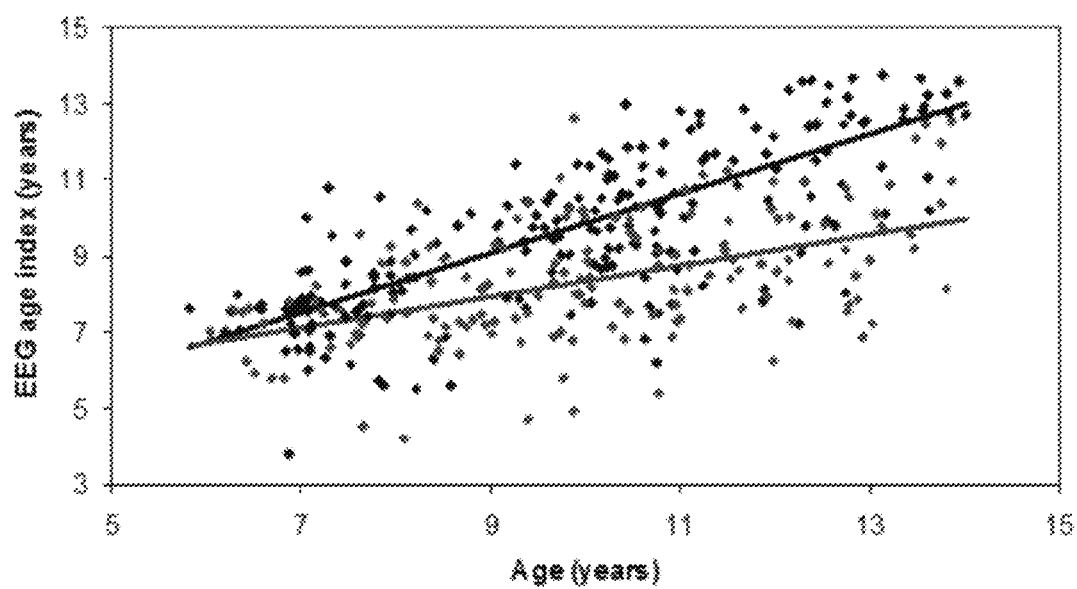
FIG. 2. The brain maturity age (BMA) based on data from individuals in an EEG database from Mentis Cura. The results for healthy subjects are shown in blue. A blue development line gives an indication on how BMA should change with age. The BMA was also calculated for the ADHD subjects in the database shown in red, with the corresponding development line also in red. Each dot represents a subject.

The difference between normal and delayed brain development, assessed by EEG measurements, is illustrated in FIG. 2. Brains of healthy normal subjects develop normally, while brains of subjects diagnosed with ADHD show a delayed development, i.e. the BMA is less than the actual age. As shown in FIG. 2, the normal BMA compared to age of subjects follows the blue line with a slope of 0.78. The blue development line is based on a data set of 216 healthy control subjects and is calculated using a so-called robust fit, which is not as much affected by outliers as the typical least squares fit. When the BMA is calculated for the ADHD subjects (data set of 150 in the database, red line), then the slope is smaller (0.41) than the slope of the blue line. This indicates that the rate of development in the cortical activity is slower with age for this group of individuals.

Changes in BMA for a Group of ADHD Boys Over 13 Weeks of Krill Oil Treatment

Figure 3:
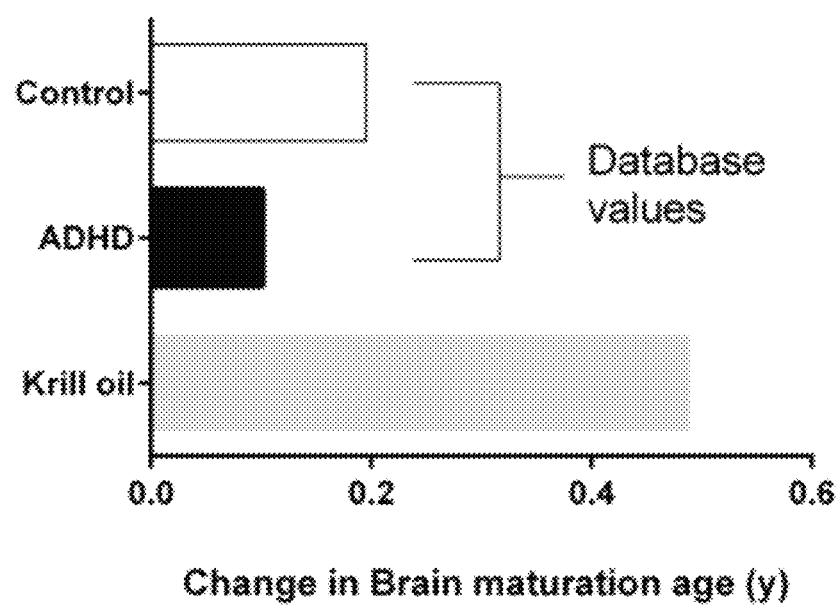
FIG. 3. The change in BMA after a period of 13 weeks. The expected change in BMA for the Normal group and ADHD group from the Mentis Cura EEG database is calculated from the slope of the lines in FIG. 2. The change in BMA for the krill oil group is the average change in BMA listed in table 2.

The age and BMA of each participant before (visit 1) and after (visit 2) 13 weeks of krill oil treatment are presented in Table 2. The average change in BMA of the 18 participants who completed the study was 0.49 years (FIG. 3) and 13 out of the 18 (72%) showed an increase in BMA. The expected change in BMA over the same time period for the normal and ADHD groups in the Mentis Cura database can be calculated from the slopes of the lines in FIG. 2. The expected change in BMA for the normal group is 0.19 years and 0.10 years for the ADHD group (FIG. 3). Therefore the observed increase in BMA for the group of ADHD boys who received the krill oil treatment over 13 weeks was 4.9 times higher than what is expected for the ADHD group in the Mentis Cura database. Furthermore, this increase in BMA is 2.6 times than what is expected for the normal group in the Mentis Cura database.

TABLE 2

Age and brain maturity age of subjects before and after krill oil treatment of 13 weeks given in years (y). Mean values are shown in the bottom line (n = 18). In all cases the actual age increases by 0.25 years.

| Visit 1 (before treatment) | | Visit 2 (after treatment) | | |
| --- | --- | --- | --- | --- |
| Actual age (y) | Brain maturation age (y) | Actual age (y) | Brain maturation age (y) | Δ Brain maturation age (y) |
| 7.07 | 6.07 | 7.32 | 5.76 | −0.31 |
| 7.12 | 6.33 | 7.37 | 7.36 | 1.03 |
| 7.46 | 7.31 | 7.71 | 7.17 | −0.14 |
| 7.46 | 7.11 | 7.71 | 6.76 | −0.35 |
| 8.09 | 9.04 | 8.34 | 9.64 | 0.60 |
| 8.33 | 6.30 | 8.58 | 6.49 | 0.19 |
| 8.34 | 7.44 | 8.59 | 6.95 | −0.49 |
| 8.52 | 5.46 | 8.77 | 6.48 | 1.02 |
| 8.59 | 6.92 | 8.84 | 7.73 | 0.81 |
| 8.73 | 6.02 | 8.98 | 6.43 | 0.41 |
| 8.74 | 7.08 | 8.99 | 7.16 | 0.08 |
| 9.61 | 7.04 | 9.86 | 7.12 | 0.08 |
| 9.86 | 10.25 | 10.11 | 10.08 | −0.17 |
| 10.16 | 7.00 | 10.41 | 7.09 | 0.09 |
| 10.46 | 7.09 | 10.71 | 7.57 | 0.48 |
| 10.84 | 7.49 | 11.09 | 7.89 | 0.40 |
| 11.36 | 8.03 | 11.61 | 11.03 | 3.00 |
| 12.04 | 6.79 | 12.29 | 8.71 | 1.92 |
| 9.04 | 7.15 | 9.29 | 7.63 | 0.49 |

Interviews

Figure 4:
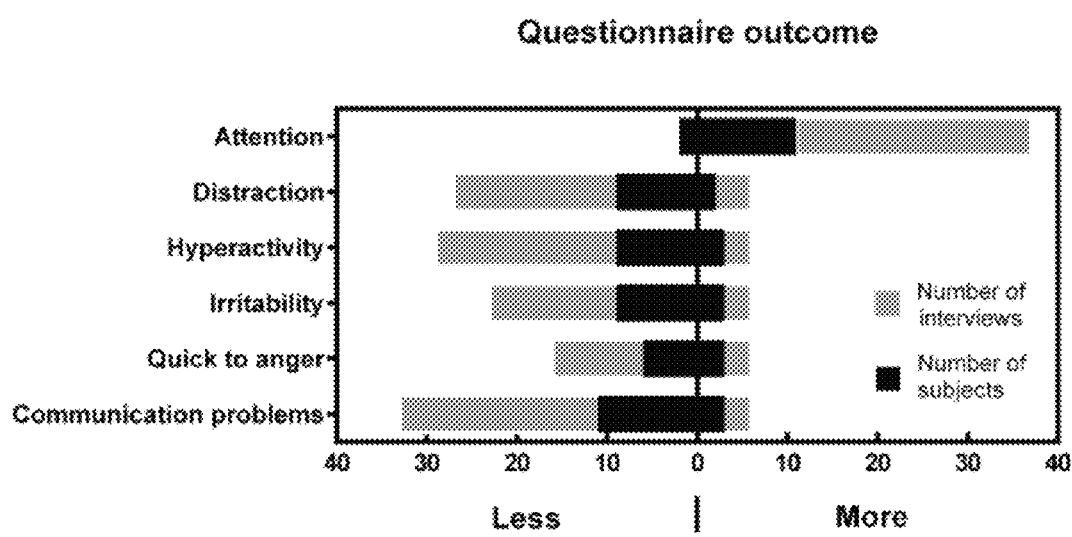
FIG. 4. Results of study interviews. The total number of interviews was 108 (n=18).

In addition to EEG measurements, subjects participating in the study and their respective parents or guardians were interviewed 6 times during the study. This resulted in a total of 108 interviews. A total of 17 participants reported positive effects of krill oil in 67 different interviews, and 6 individuals reported negative effects in 19 out of 108 interviews (Table 3). Hence, there were 62.0% positive experiences, and 17.6% negative experiences throughout the study. The outcome of the parents/guardians interviews is shown in FIG. 4. Overall, there were more positive than negative feedbacks in the 6 categories of questions. The most pronounced effect of krill oil was on attention, were parents/guardians reported that 11 participants had more attention in 37 interviews, and 2 participants were reported to have less attention in 2 interviews.

TABLE 3

Results of study interviews

| | Number of individuals | Number of interviews |
| --- | --- | --- |
| Felt positive effects | 17 | 67 |
| Felt negative effects | 6 | 19 |

The total number of interviews was 108 (n = 18).

Discussion

The present study was of interest, since several pre-clinical and clinical pharmacodynamic studies show an increased brain uptake of long-chain PUFAs when provided in phospholipid (versus methyl ester or triglyceride) form, such as the omega-3 phospholipids in krill oil [8].

One of the main findings after 13 weeks of krill oil intake was an increase in omega-3 index by 27% in ADHD boys between 7-12 y of age. The lower than normal omega-3 fatty acid levels reported earlier in ADHD patients [4, 5], might have made the individuals particularly responsive to krill oil treatment and lead to a substantial increase of the omega-3 index. It was suggested in other studies that omega-3 fatty acids are able to increase synaptic growth and function [31-33]. By accumulating omega-3 phospholipids from krill oil into glial and neuronal membranes they may not only influence membrane fluidities and integrated membrane proteins, but also intracellular gene expression, neurotransmitter metabolism and synaptic vesicle transport as was suggested in previous omega-3 studies [34-36]. Moreover, increases of omega-3 levels in red blood cells were correlated previously with better behavior in children [37-40] and also the present study found improved attention-deficit/hyperactivity symptoms after krill oil supplementation. The 6 different ADHD parameters that were positively influenced were attention, distraction, hyperactivity, irritability, proneness to anger and communication problems reported by parents, guardians and participants in interviews.

Noteworthy are several studies on neurological disorders that favor EPA over DHA supplementation for the improvement of children's behavior [12, 38, 39, 41-44]. Krill oil is characterized by an EPA to DHA ratio of 2 to 1, providing daily 524 mg of EPA to the study participants in addition to 264 mg of DHA (Table 1).

Last of all, the results were underlined by EEG measurements assessing the BMA. In this study, krill oil treatment over 13 weeks was able to increase the BMA about 5 times more than expected for ADHD subjects. Thus, krill oil supplementation can compensate for delayed brain development as reflected by EEG assessments.

CONCLUSIONS

Krill oil supplementation shows promise to improve executive functioning, in particular in addition to standard ADHD management.

1. Monastra V J, Lubar J F, Linden M: The development of a quantitative electroencephalographic scanning process for attention deficit-hyperactivity disorder: reliability and validity studies. *Neuropsychology* 2001, 15:136-144.
2. APA: *American Psychiatric Association: Diagnostic and statistical manual of mental disorders. DSM-IV-TR.* 4th edn: American Psychiatric Association; 2000.
3. Antalis C J, Stevens L J, Campbell M, Pazdro R, Ericson K, Burgess J R: Omega-3 fatty acid status in attention-deficit/hyperactivity disorder. *Prostaglandins, leukotrienes, and essential fatty acids* 2006, 75:299-308.
4. Burgess J R, Stevens L, Zhang W, Peck L: Long-chain polyunsaturated fatty acids in children with attention-deficit hyperactivity disorder. *Am J Clin Nutr* 2000, 71:327S-330S.
5. Colter A L, Cutler C, Meckling K A: Fatty acid status and behavioural symptoms of attention deficit hyperactivity disorder in adolescents: a case-control study. *Nutr J* 2008, 7:8. 278
6. Ross B M, McKenzie I, Glen I, Bennett C P: Increased levels of ethane, a non-invasive marker of n-3 fatty acid oxidation, in breath of children with attention deficit hyperactivity disorder. *Nutr Neurosci* 2003, 6:277-281.
7. Salem N, Jr., Litman B, Kim H Y, Gawrisch K: Mechanisms of action of docosahexaenoic acid in the nervous system. *Lipids* 2001, 36:945-959.
8. Burri L, Hoem N, Banni S, Berge K: Review. Marine omega-3 phospholipids: metabolism and biological activities. *Int J Mol Sci* 2012, 13:15401-15419.
9. Chalon S: The role of fatty acids in the treatment of ADHD. *Neuropharmacology* 2009, 57:636-639.
10. Raz R, Gabis L: Essential fatty acids and attention-deficit-hyperactivity disorder: a systematic review. *Dev Med Child Neurol* 2009, 51:580-592. 289
11. Schuchardt J P, Huss M, Stauss-Grabo M, Hahn A: Significance of long-chain polyunsaturated fatty acids (PUFAs) for the development and behaviour of children. *Eur J Pediatr* 2010, 169:149-164.
12. Vaisman N, Kaysar N, Zaruk-Adasha Y, Pelled D, Brichon G, Zwingelstein G, Bodennec J: Correlation between changes in blood fatty acid composition and visual sustained attention performance in children with inattention: effect of dietary n-3 fatty acids containing phospholipids. *Am J Clin Nutr* 2008, 87:1170-1180.
13. Di Marzo V, Griinari M, Carta G, Murru E, Ligresti A, Cordeddu L, Giordano E, Bisogno T, Collu M, Batetta B, et al: Dietary krill oil increases docosahexaenoic acid and reduces 2-arachidonoylglycerol but not N-acylethanolamine levels in the brain of obese Zucker rats. *Int Dairy J* 2010, 20:231-235.
14. Graf B A, Duchateau G S, Patterson A B, Mitchell E S, van Bruggen P, Koek J H, Melville S, Verkade H J: Age dependent incorporation of 14C-DHA into rat brain and body tissues after dosing various 14C-DHA-esters. *Prostaglandins Leukot Essent Fatty Acids* 2010, 83:89-96.
15. Wijendran V, Huang M C, Diau G Y, Boehm G, Nathanielsz P W, Brenna J T: Efficacy of dietary arachidonic acid provided as triglyceride or phospholipid as substrates for brain arachidonic acid accretion in baboon neonates. *Pediatr Res* 2002, 308 51:265-272.
16. Arns M, Gunkelman J, Breteler M, Spronk D: EEG phenotypes predict treatment outcome to stimulants in children with ADHD. *Journal of integrative neuroscience* 2008, 7:421-438.
17. Sumich A, Matsudaira T, Gow R V, Ibrahimovic A, Ghebremeskel K, Crawford M, Taylor E: Resting state electroencephalographic correlates with red cell long-chain fatty acids, memory performance and age in adolescent boys with attention deficit hyperactivity disorder. *Neuropharmacology* 2009, 57:708-714.
18. Chabot R J, Serfontein G: Quantitative electroencephalographic profiles of children with attention deficit disorder. *Biological psychiatry* 1996, 40:951-963.
19. Kovatchev B, Cox D, Hill R, Reeve R, Robeva R, Loboschefski T: A psychophysiological marker of attention deficit/hyperactivity disorder (ADHD)—defining the EEG consistency index. *Applied psychophysiology and biofeedback* 2001, 26:127-140.
20. Magee C A, Clarke A R, Barry R J, McCarthy R, Selikowitz M: Examining the diagnostic utility of EEG power measures in children with attention deficit/hyperactivity disorder. *Clinical neurophysiology: official journal of the International Federation of Clinical Neurophysiology* 2005, 116:1033-1040.
21. Mann C A, Lubar J F, Zimmerman A W, Miller C A, Muenchen R A: Quantitative analysis of EEG in boys with attention-deficit-hyperactivity disorder: controlled study with clinical implications. *Pediatric neurology* 1992, 8:30-36.
22. Wolosin S M, Richardson M E, Hennessey J G, Denckla M B, Mostofsky S H: Abnormal cerebral cortex structure in children with ADHD. *Human brain mapping* 2009, 30:175-184.
23. Sowell E R, Thompson P M, Welcome S E, Henkenius A L, Toga A W, Peterson B S: Cortical abnormalities in children and adolescents with attention-deficit hyperactivity disorder. *Lancet* 2003, 362:1699-1707.
24. Qiu A, Crocetti D, Adler M, Mahone E M, Denckla M B, Miller M I, Mostofsky S H: Basal ganglia volume and shape in children with attention deficit hyperactivity disorder. *The American journal of psychiatry* 2009, 166:74-82.
25. Plessen K J, Bansal R, Zhu H, Whiteman R, Amat J, Quackenbush G A, Martin L, Durkin K, Blair C, Royal J, et al: Hippocampus and amygdala morphology in attention-deficit/hyperactivity disorder. *Archives of general psychiatry* 2006, 63:795-807.
26. Barry R J, Clarke A R, McCarthy R, Selikowitz M, Johnstone S J, Hsu C I, Bond D, Wallace M J, Magee C A: Age and gender effects in EEG coherence: II. Boys with attention deficit/hyperactivity disorder. *Clinical neurophysiology: official journal of the International Federation of Clinical Neurophysiology* 2005, 116:977-984.
27. Thatcher R W, North D M, Biver C J: Development of cortical connections as measured by EEG coherence and phase delays. *Human brain mapping* 2008, 348 29:1400-1415.
28. Shaw P, Eckstrand K, Sharp W, Blumenthal J, Lerch J P, Greenstein D, Clasen L, Evans A, Giedd J, Rapoport J L: Attention-deficit/hyperactivity disorder is characterized by a delay in cortical maturation. *Proceedings of the National Academy of Sciences of the United States of America* 2007, 104:19649-19654.
29. Kaufmann J, Birmaher B, Brent D, Rao U, Ryan N: Kiddie-SADS-Present and lifetime version (*K-SADS-PL*, version 1.0). Pittsburgh, Pa.: University of Pittsburgh School of Medicine; 1996.
30. Gudmundsson S, Runarsson T P, Sigurdsson S, Eiriksdottir G, Johnsen K: Reliability of quantitative EEG features. *Clinical neurophysiology: official journal of the International Federation of Clinical Neurophysiology* 2007, 118:2162-2171.
31. Cao D, Kevala K, Kim J, Moon H S, Jun S B, Lovinger D, Kim H Y: Docosahexaenoic acid promotes hippocampal neuronal development and synaptic function. *J Neurochem* 2009, 111:510-521. 362 12
32. Kim H Y, Moon H S, Cao D, Lee J, Kevala K, Jun S B, Lovinger D M, Akbar M, Huang BX: N-Docosahexaenoylethanolamide promotes development of hippocampal neurons. *Biochem J* 2011, 435:327-336.
33. Su H M: Mechanisms of n-3 fatty acid-mediated development and maintenance of learning memory performance. *J Nutr Biochem* 2010, 21:364-373.
34. Drevon C A: Marine oils and their effects. *Nutr Rev* 1992, 50:38-45.
35. Levant B, Ozias M K, Carlson S E: Sex-specific effects of brain LC-PUFA composition on locomotor activity in rats. *Physiol Behav* 2006, 89:196-204.
36. Chalon S, Vancassel S, Zimmer L, Guilloteau D, Durand G: Polyunsaturated fatty acids and cerebral function: focus on monoaminergic neurotransmission. *Lipids* 372 2001, 36:937-944.

37. Stevens L, Zhang W, Peck L, Kuczek T, Grevstad N, Mahon A, Zentall S S, Arnold L E, Burgess J R: EFA supplementation in children with inattention, hyperactivity, and other disruptive behaviors. *Lipids* 2003, 38:1007-1021.
38. Beblo S, Reinhardt H, Demmelmair H, Muntau A C, Koletzko B: Effect of fish oil supplementation on fatty acid status, coordination, and fine motor skills in children with phenylketonuria. *J Pediatr* 2007, 150:479-484.
39. Wozniak J, Biederman J, Mick E, Waxmonsky J, Hantsoo L, Best C, Cluette-Brown J E, Laposata M: Omega-3 fatty acid monotherapy for pediatric bipolar disorder: a prospective open-label trial. *Eur Neuropsychopharmacol* 2007, 17:440-447.
40. Itomura M, Hamazaki K, Sawazaki S, Kobayashi M, Terasawa K, Watanabe S, Hamazaki T: The effect of fish oil on physical aggression in schoolchildren—a randomized, double-blind, placebo-controlled trial. *J Nutr Biochem* 2005, 16:163-385 171.
41. Amminger G P, Berger G E, Schafer M R, Klier C, Friedrich M H, Feucht M: Omega-3 fatty acids supplementation in children with autism: a double-blind randomized, placebo-controlled pilot study. *Biol Psychiatry* 2007, 61:551-553.
42. Nemets H, Nemets B, Apter A, Bracha Z, Belmaker R H: Omega-3 treatment of childhood depression: a controlled, double-blind pilot study. *Am J Psychiatry* 2006, 163:1098-1100.
43. Richardson A J, Montgomery P: The Oxford-Durham study: a randomized, controlled trial of dietary supplementation with fatty acids in children with developmental coordination disorder. *Pediatrics* 2005, 115:1360-1366.
44. Sinn N, Bryan J: Effect of supplementation with polyunsaturated fatty acids and micronutrients on learning and behavior problems associated with child ADHD. *J Dev Behav Pediatr* 2007, 28:82-91.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

The invention claimed is:

1. A method of improving or supporting brain maturity age in a subject in need thereof comprising:
administering an omega-3 phospholipid supplement to said subject under conditions such that the brain maturity age of the subject is improved, wherein said brain maturation age is calculated by comparison of EEG measurements with reference EEG measurements.
2. The method of claim 1, wherein said omega-3 phospholipid supplement is a krill oil, fish oil, fish roe oil, or fish byproduct oil.
3. The method of claim 2, wherein said krill oil comprises from about 35% to 60% phospholipids on a w/w basis; from about 20% to 45% triglycerides on a w/w basis; and from about 50 to about 2500 mg/kg astaxanthin.
4. The method of claim 1, wherein said omega-3 phospholipid supplement comprises EPA and DHA.
5. The method of claim 1, wherein said subject is an adolescent.
6. The method of claim 5, wherein said adolescent is a male.
7. The method of claim 1, wherein said administration is oral.
8. The method of claim 1, wherein said omega-3 phospholipid supplemented is administered a daily dosage of from about 3 grams to about 6 grams per day.
9. The method of claim 8, wherein said daily dose is administered in two doses of from 1.5 to 3 grams in the morning and evening.
10. The method of claim 1, wherein said subject has been diagnosed with ADHD.
11. A method of improving or supporting brain maturity age in a subject in need thereof comprising:
administering a krill oil supplement to said subject under conditions such that the brain maturity age of the subject is improved, wherein said krill oil supplement comprises from about 35% to 60% phospholipids on a w/w basis, from about 20% to 45% triglycerides on a w/w basis, and from about 50 to about 2500 mg/kg astaxanthin, and wherein said brain maturation age is calculated by comparison of EEG measurements with reference EEG measurements.
12. The method of claim 11, wherein said subject is an adolescent male.
13. The method of claim 11, wherein said administration is oral.
14. The method of claim 11, wherein said omega-3 phospholipid supplemented is administered a daily dosage of from about 3 grams to about 6 grams per day.
15. The method of claim 14, wherein said daily dose is administered in two doses of from 1.5 to 3 grams in the morning and evening.

* * * * *